United States Patent
Nukui (10) Patent No.: US 7,085,345 B2
(45) Date of Patent: Aug. 1, 2006

(54) RADIATION COMPUTED TOMOGRAPHIC IMAGING APPARATUS AND RADIATION DETECTOR FOR USE THEREIN

(75) Inventor: Masatake Nukui, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/940,848

(22) Filed: Sep. 14, 2004

(65) Prior Publication Data

US 2005/0074087 A1    Apr. 7, 2005

(30) Foreign Application Priority Data

Sep. 19, 2003  (JP) .............................. 2003-328260

(51) Int. Cl.
  *A61B 6/00*  (2006.01)
  *G21K 1/02*  (2006.01)

(52) U.S. Cl. .............................. 378/19; 378/4; 378/147

(58) Field of Classification Search .................... 378/4, 378/7, 19, 86, 98.8, 147–154; 250/363.1, 250/370.09
See application file for complete search history.

(56) References Cited

U.S. PATENT DOCUMENTS

| 4,991,189 A | 2/1991 | Boomgaarden et al. |
| 5,054,041 A | 10/1991 | Hampel |
| 5,644,614 A | 7/1997 | Toth et al. |
| 5,657,364 A * | 8/1997 | Pfoh .......................... 378/137 |
| 6,134,301 A | 10/2000 | Mruzek et al. |
| 6,173,039 B1 | 1/2001 | Hampel et al. |
| 6,175,609 B1 * | 1/2001 | Edic et al. ..................... 378/7 |
| 6,256,364 B1 | 7/2001 | Toth et al. |
| 6,266,434 B1 | 7/2001 | Toth et al. |
| 6,298,117 B1 | 10/2001 | Hampel et al. |
| 6,304,626 B1 * | 10/2001 | Adachi et al. ................ 378/19 |
| 6,396,902 B1 | 5/2002 | Tybinkowski et al. |
| 6,408,049 B1 | 6/2002 | Edic et al. |
| 6,449,340 B1 | 9/2002 | Tybinkowski et al. |
| 6,470,067 B1 | 10/2002 | Harding |
| 6,580,939 B1 | 6/2003 | Chaney et al. |

(Continued)

FOREIGN PATENT DOCUMENTS

| JP | 06-022949 | 2/1994 |
| JP | 2000-093418 | 4/2000 |

OTHER PUBLICATIONS

European Patent Office Search Report; 154282/10236; 04255643.1-2305-; GE Medical Systems Global Technology Company LLC; 3 pgs.

(Continued)

*Primary Examiner*—Edward J. Glick
*Assistant Examiner*—Irakli Kiknadze
(74) *Attorney, Agent, or Firm*—Carl B. Horton, Esq.; Armstrong Teasdale LLP (57) ABSTRACT

An apparatus for reducing the influence by scatter rays and improving image quality of a tomographic image. The apparatus includes an X-ray detector and a calculation/control apparatus for generating tomographic image data for a tomographic image of the subject based on the projection data. The X-ray detector includes a plurality of detector channels for detecting the radiation, extending in a two-dimensional manner in two arrangement directions, i.e., in channel and column directions, the channel direction being contained in a plane of rotation of the X-ray source, the column direction being orthogonal to the channel direction and aligned along the axis of rotation; and collimators for confining an angle at which X-rays impinge upon the detector channels, provided at borders between the detector channels adjoining in the column direction.

20 Claims, 8 Drawing Sheets

U.S. PATENT DOCUMENTS

6,652,143 B1    11/2003    Popescu
6,744,852 B1    6/2004    Klotz et al.
6,934,354 B1*    8/2005    Hoffman ...................... 378/19
6,993,110 B1*    1/2006    Hoffman ...................... 378/19
2003/0076929 A1*    4/2003    Hoheisel et al. ........... 378/98.8

OTHER PUBLICATIONS

Endo Masahiro et al; "Effect of Scattered Radiation on Image Noise in Cone Beam CT"; Med. Phys. 28 (4), Apr. 2001; pp. 469-474.

* cited by examiner

RADIATION COMPUTED TOMOGRAPHIC IMAGING APPARATUS AND RADIATION DETECTOR FOR USE THEREIN

CROSS REFERENCE TO RELATED APPLICATIONS

This application claims the benefit of Japanese Application No. 2003-328260 filed Sep. 19, 2003.

BACKGROUND OF THE INVENTION

The present invention relates to a radiation computed tomographic imaging apparatus such as an X-ray CT (computed tomography) apparatus. More particularly, the present invention relates to a radiation computed tomography apparatus capable of acquiring volume data, such as a VCT (volume CT) apparatus or a multi-row CT apparatus, and a radiation detector for use in such an apparatus.

Known X-ray CT apparatuses include, for example, one that acquires projection data for a subject by an X-ray detector having a plurality of X-ray detector channels arranged in a two-dimensional manner. The plurality of X-ray detector channels are positioned to have their width in a direction along a predefined axis with respect to the subject. Since X-ray detector channel rows are formed over a certain width in the axis direction, the X-ray detector having X-ray detector channels arranged in a two-dimensional manner is generally referred to as a multi-row detector.

In the multi-row detector, a direction along the axis is sometimes referred to as a column direction, and a direction orthogonal to the column direction as a channel direction, for example.

In the X-ray CT apparatus comprising the multi-row detector, projection data of a cross section of the subject is collected by emitting an X-ray fan beam, which has an extent in both the column and channel directions, from a predefined focal spot at a plurality of positions around the axis to the multi-row detector.

A tomographic image of the subject is produced by a reconstruction calculation based on the projection data.

Patent Document 1 discloses an X-ray CT apparatus having an X-ray detector provided with collimators for the X-ray detector channels, which collimators are arranged in the channel direction and directed toward a focal spot of an X-ray fan beam.

In the X-ray detector described in Patent Document 1, each X-ray detector channel is disposed in the channel direction to have its detecting surface for detecting X-rays directed toward the focal spot.

[Patent Document 1] Japanese Patent Application Laid Open No. H6-22949.

In the imaging using an X-ray CT apparatus, there is a possibility that the detecting surfaces in the X-ray detector may be struck also by X-rays other than those directly impinging upon the detecting surfaces from a focal spot, i.e., for example, by scatter X-rays (scatter rays), which are caused by X-rays having their direction of travel deflected due to collision with an object, such as bone, in the subject. The scatter rays contain projection information on the subject that the X-ray detector channels receiving the scatter rays should not detect. Therefore, the scatter rays cause generation of artifacts, and image quality of the tomographic image may be degraded.

Since the X-ray CT apparatus disclosed in Patent Document 1 has the collimators in the channel direction, scatter rays can be prevented from impinging upon the detecting surfaces to some extent.

However, when the detector channels are arranged in more than one row and a fan beam is used to acquire projection data, the X-ray fan beam must have a larger width. The increase in the width of the X-ray fan beam causes X-rays to impinge upon more divergent positions in the subject, thus increasing the probability of generation of scatter rays. It is therefore difficult for a collimator merely provided at each X-ray detector channel in the channel direction, as in the X-ray CT apparatus described in Patent Document 1, to effectively prevent scatter rays from impinging upon the detecting surface. Consequently, image quality is more likely degraded.

SUMMARY OF THE INVENTION

It is therefore an object of the present invention to provide a radiation computed tomographic imaging apparatus capable of more effectively reducing the influence by scatter rays, and improving image quality of a tomographic image.

It is another object of the present invention to provide a radiation detector for use in a radiation computed tomographic imaging apparatus, capable of more effectively reducing the influence by scatter rays, and improving image quality of a tomographic image.

A radiation computed tomographic imaging apparatus, in accordance with the present invention, comprises: a radiation source for emitting radiation while rotating around a predefined axis of rotation; a radiation detector for detecting said radiation passing through a subject around said axis of rotation, said radiation detector having a plurality of radiation detector elements for detecting said radiation, extending in a two-dimensional manner in first and second arrangement directions, said first arrangement direction being contained in a plane of rotation of said radiation source, said second arrangement direction being orthogonal to said first arrangement direction and aligned along said axis of rotation; and reconstructing means for arithmetically reconstructing tomographic image data for a tomographic image of said subject based on projection data of said subject obtained from said radiation detected by said radiation detector, wherein said radiation detector comprises collimators for confining an angle at which said radiation impinges upon said radiation detector elements, said collimators being provided at borders between said radiation detector elements adjoining in said second arrangement direction.

A radiation detector in accordance with the present invention is a radiation detector for use in a radiation computed tomographic imaging apparatus for generating tomographic image data for a tomographic image of a subject based on projection data of said subject obtained from radiation emitted from a radiation source rotating around a predefined axis of rotation and passing through said subject, which comprises: a plurality of radiation detector elements for detecting said radiation for acquiring said projection data, extending in a two-dimensional manner in first and second arrangement directions, said first arrangement direction being contained in a plane of rotation of said radiation source, said second arrangement direction being orthogonal to said first arrangement direction and aligned along said axis of rotation; and collimators for confining an angle at which said radiation impinges upon said radiation detector elements, provided at borders between said radiation detector elements adjoining in said second arrangement direction.

In the present invention, a radiation detector is comprised of radiation detector elements extending in a two-dimensional manner in first and second arrangement directions. The first arrangement direction is contained in a plane of rotation of a radiation source around a predefined axis of rotation, and the second arrangement direction is orthogonal to the first arrangement direction and aligned along the axis of rotation.

At the borders between the radiation detector elements adjoining in the second arrangement direction of the radiation detector, collimators are provided. The radiation emitted from the radiation source impinges upon the radiation detector elements with its angle confined by the collimators in the second arrangement direction.

Under such a condition, the radiation passing through the subject is detected by the radiation detector around the predefined axis.

According to the present invention, the influence by scatter rays is more effectively reduced, and image quality of a tomographic image can be improved.

The present invention can be applied to a computed tomographic imaging (CT) apparatus employing radiation. Moreover, the present invention can be applied to a radiation detector for use in a CT apparatus.

Further objects and advantages of the present invention will be apparent from the following description of the preferred embodiments of the invention as illustrated in the accompanying drawings.

DETAILED DESCRIPTION OF THE INVENTION

Embodiments of the present invention will now be described with reference to the accompanying drawings. It should be noted that radiation in the present invention includes X-rays. The following description will be made exemplifying an X-ray CT apparatus employing X-rays as the radiation.

Figure 1:
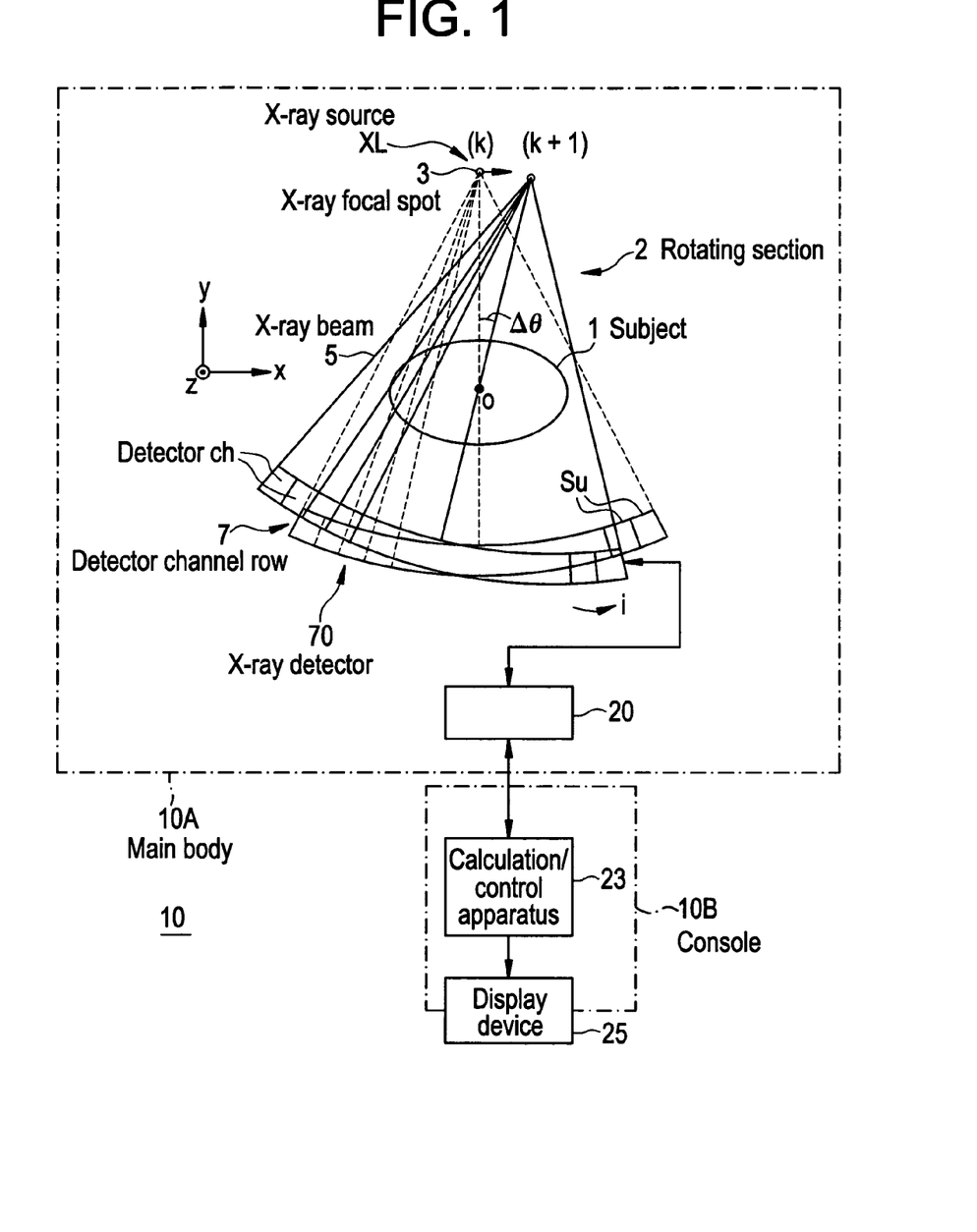
FIG. 1 is a diagram showing the general configuration of an X-ray CT apparatus in accordance with one embodiment of the present invention.

FIG. 1 is a diagram showing the general configuration of an X-ray CT apparatus in accordance with an embodiment of the present invention. The X-ray CT apparatus 10 shown in FIG. 1 comprises an X-ray CT apparatus main body 10A and a console 10B. One embodiment of the radiation computed tomography apparatus of the present invention is the X-ray CT apparatus 10 shown in FIG. 1.

The X-ray CT apparatus main body 10A comprises a rotating section 2 and a data acquisition system (DAS) 20, as shown in FIG. 1.

One embodiment of the moving means in the present invention corresponds to the rotating section 2.

The rotating section 2 comprises an X-ray source XL for emitting X-rays, and an X-ray detector 70 for detecting the X-rays emitted by the X-ray source XL.

The X-ray source XL emits a fan-shaped X-ray beam 5 from an X-ray focal spot 3. The fan-shaped X-ray beam 5 is sometimes referred to as a fan beam.

The intensity of the X-ray beam 5 is detected by an X-ray detector 70.

Figure 2:
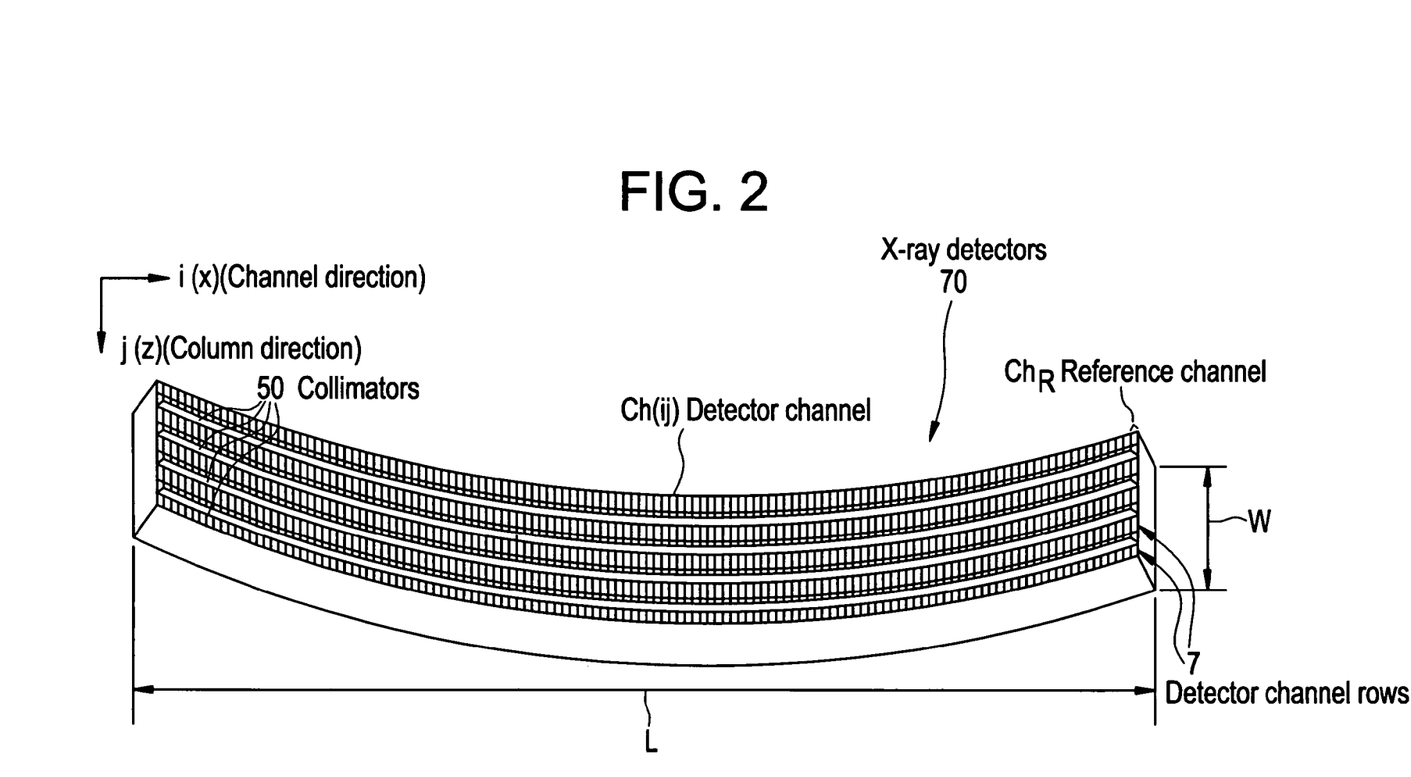
FIG. 2 is a perspective view showing the configuration of an X-ray detector for use in the X-ray CT apparatus shown in FIG. 1.

The X-ray detector 70 has a plurality of detector channels ch arranged in a two-dimensional matrix (array), as shown in FIG. 2.

An embodiment of the radiation detector elements in the present invention corresponds to the detector channels ch. Each detector channel ch is made by, for example, a combination of a scintillator and a photodiode.

The detector channels ch arranged in a two-dimensional manner are designated by a column index i along the row direction and a row index j along the column direction. The number of column indices i is of the order of 1000, and the number of row indices j is of the order of 16, for example.

The row direction is sometimes referred to as the channel direction here. The detector channels ch lined up in a row in the channel direction are together referred to as a detector channel row.

In the column direction, a plurality of detector channel rows 7 are juxtaposed to one another in parallel.

An embodiment of the first arrangement direction in the present invention corresponds to the row direction (channel direction), and an embodiment of the second arrangement direction corresponds to the column direction.

As shown in FIGS. 1 and 2, the column direction in the X-ray detector 70 is defined as the z-axis direction. A plane orthogonal to the z-axis is defined as an x-y plane.

The X-ray beam 5 is a fan beam having an extent in both the x-y and x-z planes.

A detecting surface Su of each detector channel ch can individually and independently detect X-ray intensity of the X-ray beam 5, and data corresponding to the number of the detector channels ch arranged in a two-dimensional manner can be obtained.

Detailed description on the X-ray detector 70 will be made later.

A subject 1 is positioned between the X-ray source XL and X-ray detector 70. The X-ray source XL and X-ray detector 70 of the X-ray CT apparatus 10 in accordance with the present embodiment are rotated around a predefined axis O by the rotating section 2 as shown in FIG. 1 while maintaining their positional relationship relative to each other.

An embodiment of the axis of rotation in the present invention corresponds to the axis O.

For example, the body axis direction of the subject 1 from head to toe is made to coincide with the direction of the axis O. Moreover, the direction of the axis O coincides with the z-axis direction in FIG. 1.

Collection of X-ray intensity data is achieved by a scan in which the intensity of the X-ray beam 5 passing through the subject 1 is detected by the detector channels ch in a sequentially varying direction of emission of the X-ray beam 5 toward the subject 1 while rotating the X-ray source XL and X-ray detector 70 around the axis O by the rotating section 2. Data in a plurality of directions in one rotation around the axis O are thus obtained. The direction of data collection is referred to as a view. In FIG. 1, a reference symbol k represents a view index. The number of views per rotation is of the order of 1000, for example. In this case, the spacing Δθ between the views shown in FIG. 1 is of the order of 360°/1000.

The DAS 20 collects a plurality of sets of the data acquired by the X-ray detector 70. The DAS 20 converts analog data of X-ray intensity detected by the X-ray detector 70 into digital data, and sends them to the console 10B.

The digital data sent to the console 10B represent projection data of a cross-sectional plane through which the X-ray beam 5 passes in the subject 1.

As shown in FIG. 1, the console 10B comprises a calculation/control apparatus 23 and a display device 25.

One embodiment of the reconstructing means in the present invention corresponds to the calculation/control apparatus 23.

The calculation/control apparatus 23 is implemented by hardware, such as a CPU (central processing unit), and software for driving the hardware, for example.

The calculation/control apparatus 23 receives the projection data collected by the DAS 20. The calculation/control apparatus 23 performs a reconstruction calculation, such as backprojection, based on the received projection data to generate image data. The image data generated based on the projection data represents an image of a cross section through which the X-ray beam 5 passes in the subject 1, i.e., image data for a tomographic image (tomographic image data).

Moreover, the calculation/control apparatus 23 controls the X-ray CT apparatus 10 for tomographic image production to execute operations including rotation of the X-ray source XL and X-ray detector 70 by the rotating section 2 and acquisition of projection data via the DAS 20.

Furthermore, the calculation/control apparatus 23 conducts control for displaying the produced tomographic image on the display device 25, such as a CRT (cathode-ray tube) or a liquid crystal display panel. The display device 25 also displays an operation image for operating the X-ray CT apparatus 10.

The calculation/control apparatus 23 is connected with an input device, such as a keyboard (not shown). Instructions from a human operator operating the X-ray CT apparatus 10 are input to the calculation/control apparatus 23 via the input device.

The X-ray detector 70 in the present embodiment will now be described in detail.

As shown in FIG. 2, the X-ray detector 70 having the plurality of detector channels ch arranged in a two-dimensional manner forms a curve along the direction of rotation of the X-ray source XL and X-ray detector 70 around the axis O. In this case, the X-ray detecting surface Su of each detector channel ch is directed toward the X-ray focal spot 3 in the channel direction.

The channel direction may be regarded as a direction contained in a plane of rotation of the X-ray source XL and X-ray detector 70 around the axis O.

On the other hand, in the column direction orthogonal to the channel direction and along the z-axis direction, the detector channels ch are straightly arranged in a direction parallel to the z-axis. Thus, the detecting surfaces Su are not all directed toward the X-ray focal spot 3, but uniformly face in different directions, one of which is the X-ray focal spot 3 direction.

The length L of the X-ray detector 70 in the channel direction shown in FIG. 2 is of the order of 1000 mm, for example.

The length W in the column direction is of the order of 30–50 mm, for example. However, the length W may increase with an increase in the number of detector channel rows 7.

In the present embodiment, the X-ray detector 70 is provided with collimators 50 extending in the channel direction, at the borders between the detector channels ch adjoining in the column direction.

Each collimator 50 is formed in a rectangular plate, for example. Each collimator 50 is directed in a direction normal to the detecting surfaces Su, for example.

It should be noted that although an apparatus (not shown) provided near the X-ray focal spot 3 for fan-shaping the X-ray beam 5 is also sometimes referred to in the art as a collimator, the collimators 50 in the present embodiment are different from that collimator for shaping the X-ray beam 5.

Figure 3:
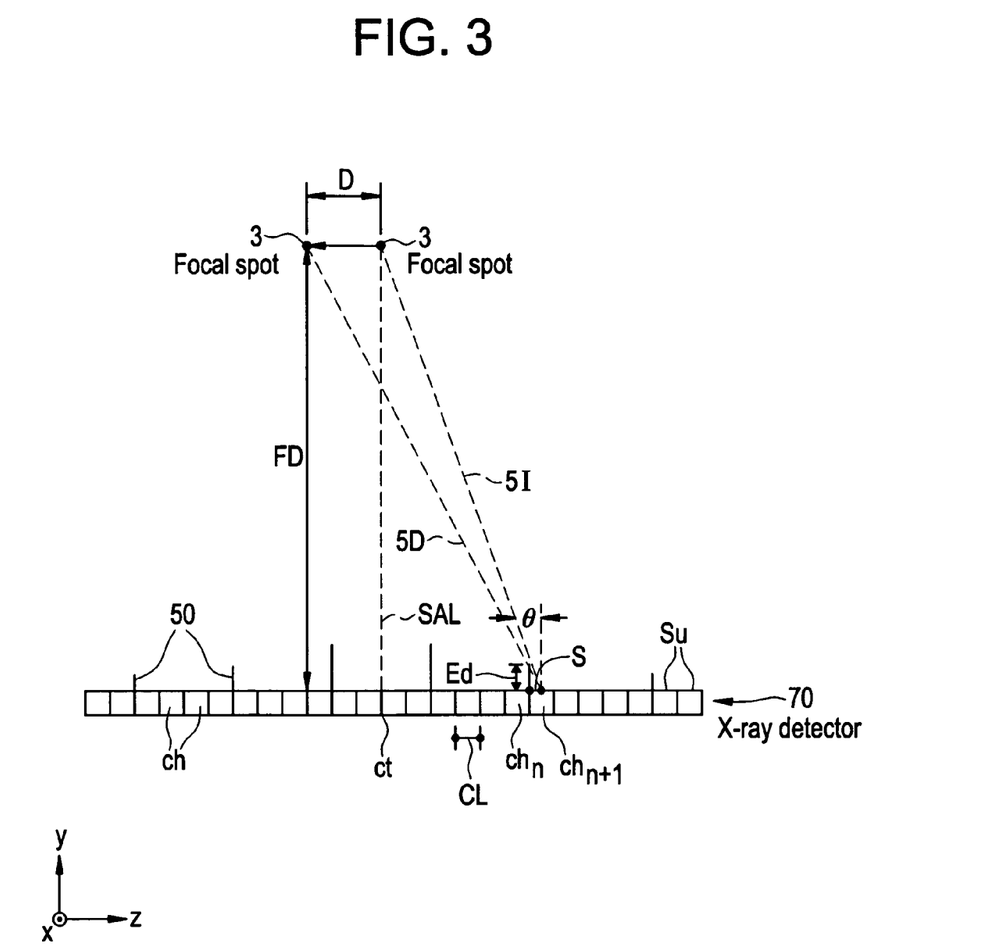
FIG. 3 is a schematic diagram showing the positional relationship between the X-ray focal spot and X-ray detector as viewed in the x-axis direction in FIG. 1.

FIG. 3 is a diagram showing the positional relationship between the X-ray focal spot 3 and X-ray detector 70 as viewed in the x-axis direction in FIG. 1. It should be noted that FIG. 3 is illustrative, and the scale is not an actual one.

By providing the aforementioned collimators 50, the incident angle of X-rays on the detecting surfaces Su is confined in the column direction. Therefore, scatter X-rays (scatter rays) are less likely to impinge upon the detecting surfaces Su and be detected, and the influence by scatter rays is reduced. The scatter rays are caused by X-rays having their direction of travel deflected due to collision with an object in the subject 1 that has extremely different X-ray permeability, such as bone. Therefore, it can be considered that some scatter rays will always be generated in imaging the subject 1. As an increase in the number of rows in the X-ray detector 70 enlarges the width of the X-ray beam 5 in the column direction, the X-ray beam 5 is directed onto a wider area in the subject 1, resulting in generation of more scatter rays and accordingly an increase in the probability that the detector channels ch pick up scatter rays.

From the viewpoint of causing only X-rays directly reaching detector channels ch from the X-ray focal spot 3 to impinge upon the detecting surfaces Su, and blocking scatter rays by the collimators 50, the collimators 50 are preferably constructed by using a material of high X-ray absorptivity such as tungsten.

However, too many collimators 50 may reduce efficiency of X-ray usage because X-rays that would otherwise directly impinge upon the detecting surfaces Su are blocked by the collimators 50.

Thus, in the present embodiment, the collimators 50 are provided at predetermined intervals in the column direction, as exemplarily shown in FIG. 3. For example, the collimators 50 are provided at regular intervals in the column direction.

The interval between the collimators 50 is preferably of the order of 10–20 mm, for example, from the viewpoint of trade-off between maintenance of efficiency of X-ray usage and reduction of scatter rays.

As shown in FIG. 3, the X-ray detector 70 in accordance with the present embodiment is configured to be symmetric in the column direction along the z-axis with respect to a line SAL connecting a midpoint ct and the X-ray focal spot 3.

Then, it is preferred that no collimator 50 be provided at the borders between the detector channels ch at and near the center ct, and the collimators 50 be provided at the borders between the detector channels ch other than those at and near the center ct. This is done for preventing the higher efficiency in X-ray usage in the detector channels ch at and near the center ct from decreasing, because the distance from the X-ray focal spot 3 to the detecting surfaces Su of the detector channels ch there is shorter than the distance to the detector channels ch lying in the outer side in the column direction, resulting the higher efficiency in X-ray usage.

By providing the collimators 50 as described above, however, when exposed to the X-ray beam 5, a shadowed portion is created by a collimator 50 in a detector channel ch that lies adjacent to that collimator 50 and on the outer side with respect to the collimator 50, as shown in FIG. 3. For example, a detector channel $ch_{n+1}$ in FIG. 3 is shadowed by the collimator 50. On the other hand, a detector channel $ch_n$ that lies adjacent to the collimator 50 and detector channel $ch_{n+1}$, and lies on the inner side with respect to the collimator 50, is not shadowed by the collimator 50.

X-rays cannot directly enter any such shadowed portion created by the collimator 50 from the X-ray focal spot 3, and efficiency of X-ray usage is reduced in the detector channel $ch_{n+1}$, for example.

Accordingly, to maintain a certain level of efficiency of X-ray usage in the detector channels ch shadowed by the collimators 50, the height of each collimator 50 is determined so that efficiency of X-ray usage exceeds a certain threshold.

The size of the shadowed portion by the collimators 50 varies depending upon the amount of drift of the X-ray focal spot 3. Therefore, the height of each collimator 50 is determined taking drift of the X-ray focal spot 3 into account. The drift of the X-ray focal spot 3 here refers to a position offset of the X-ray focal spot 3 due to, for example, thermal expansion.

The process of determining the height of each collimator 50 will now be described in detail.

Referring further to FIG. 3, the length of a perpendicular from the X-ray focal spot 3 to the X-ray detector 70 is represented as FD.

The width of one detector channel ch in the z-axis direction is represented as CL.

Moreover, the amount of drift of the X-ray focal spot 3 with respect to a reference position on a normal to the midpoint ct is represented as D. It should be noted that the amount of drift D may take both positive and negative values depending on the direction of drift of the X-ray focal spot 3.

At the reference position, an X-ray beam 5I impinges upon a detector channel $ch_{n+1}$, and an X-ray beam 5D at a drifted position impinges upon a detector channel chn.

The number of detector channels ch counted from the midpoint ct up to a detector channel ch provided with a target collimator 50 whose height is to be determined is represented as N.

The height of the target collimator 50 is represented as Ed, and the length in the z-axis direction of a shadowed portion created by the target collimator 50 is represented as S.

Obviously from FIG. 3, $S:Ed = S+D+N \cdot CL : FD$. Therefore, $(S+D+N \cdot CL)Ed = FD \cdot S$, and hence, $(D+N \cdot CL)Ed = (FD-Ed)S$.

From the equation, the length S can be obtained according to: $S = ((D+N \cdot CL)Ed)/(FD-Ed)$.

The length S is set so that efficiency of X-ray usage, $(1-S/CL)$, which is defined using the length S, exceeds a predetermined threshold. Since the width CL is constant, the value of efficiency of X-ray usage, $(1-S/CL)$, varies with the length S.

For example, since it is undesirable for efficiency of X-ray usage to be reduced by more than 5% by providing the collimator 50, the value of the length S is determined so that $0.95 < (1-S/CL) < 1$ holds when a certain amount of drift D is accounted for.

After determining the length S as described above, the height Ed of the target collimator 50 to be determined is obtained from the equation $(S+D+N \cdot CL)Ed = FD \cdot S$, as $Ed = (FD \cdot S)/(S+D+N \cdot CL)$ when a certain amount of drift D is accounted for.

Since the incident angle θ of the X-ray beam 5 on a detecting surface Su is larger on the outer side farther from the midpoint ct, and X-ray beam 5 impinges more slantingly upon the detecting surface Su there, the length S is larger for a collimator 50 having the same height Ed on the outer side.

Thus, to securely maintain efficiency of X-ray usage above the threshold by reducing the length S on the outer side, the height Ed of the collimator 50 is preferably smaller with increasing separation from the midpoint ct toward the outside, as shown in FIG. 3.

When the collimators 50 are provided as described above, the detector channel $ch_{n+1}$ with a shadow and the detector channel $ch_n$ without a shadow, for example, have different X-ray detection sensitivity.

Efficiency of X-ray usage according to the amount of X-rays impinging upon a detecting surface Su is one of the main factors that dictate the X-ray detection sensitivity in each detector channel ch.

Therefore, the calculation/control apparatus 23 in the X-ray CT apparatus 10 corrects the difference in X-ray detection sensitivity between the detector channels ch due to the collimators 50, and then reconstructs tomographic image data.

However, since the X-ray detection sensitivity also varies with the amount of drift D of the X-ray focal spot 3, the correction must be made taking the amount of drift D into account.

The process of correcting the X-ray detection sensitivity will now be described in detail.

To correct the X-ray detection sensitivity, a calibration process is conducted for determining an offset of the X-ray detection sensitivity with respect to a reference value for each detector channel ch.

Figure 4:
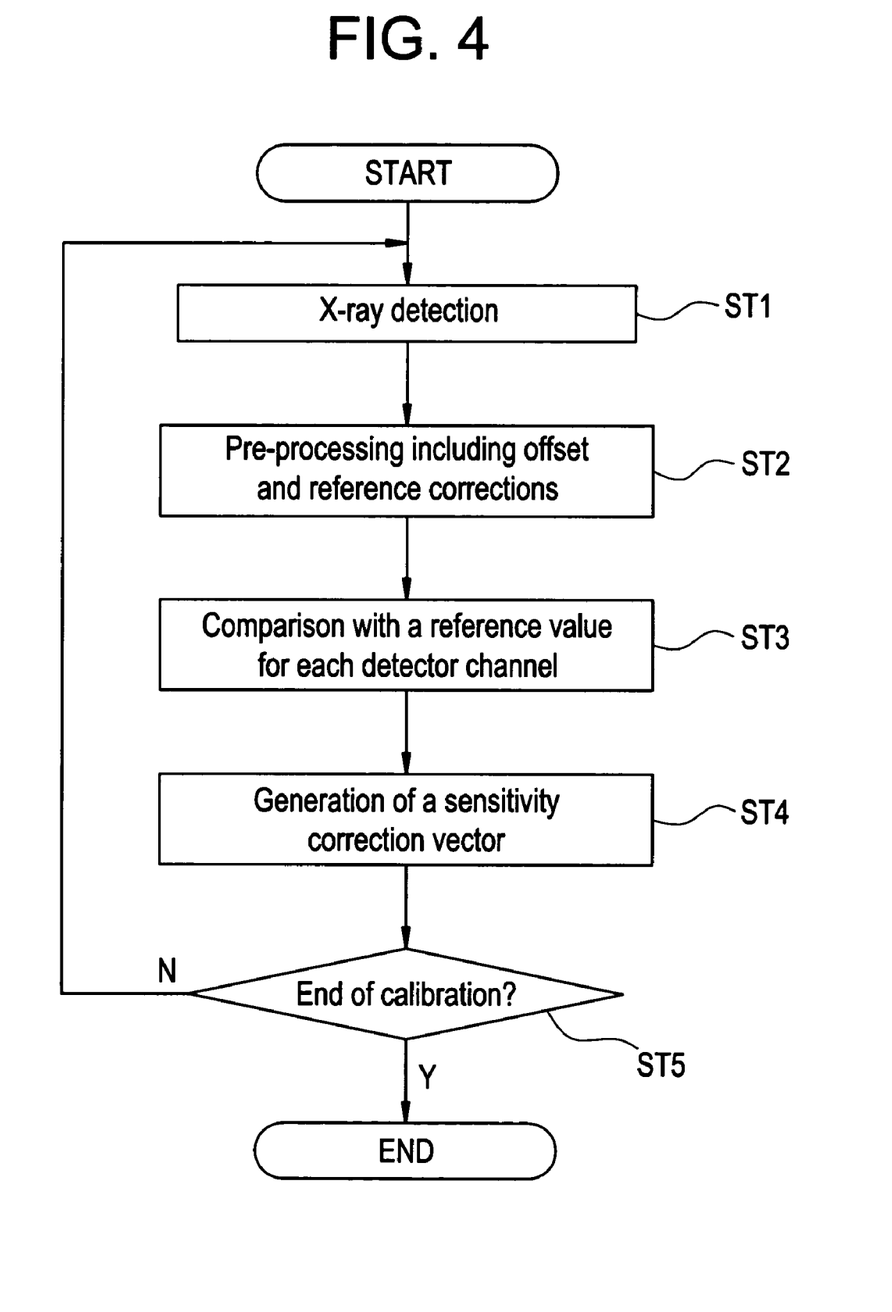
FIG. 4 is a flow chart showing an exemplary procedure of calibration for determining the amount of offset of X-ray detection sensitivity of the X-ray detector shown in FIG. 2 with respect to a reference value.

FIG. 4 is a flow chart of an exemplary procedure of the calibration.

In the calibration, X-rays are first detected by the rotating section 2 (Step ST1).

Since the detection of X-rays at Step ST1 is for the purpose of inspecting the X-ray detection sensitivity in each detector channel ch, the intensity of X-rays emitted from the X-ray source XL is detected by the X-ray detector 70 in the absence of the subject 1. Moreover, the detection need not necessarily be conducted with the rotating section 2 being rotated, and it is sufficient to detect the intensity of X-rays impinging upon the X-ray detector 70 in at least one view.

As previously discussed, detected data of the X-ray intensity detected by the X-ray detector 70 is collected by the DAS 20, and sent to the calculation/control apparatus 23.

The calculation/control apparatus 23 conducts pre-processing including offset and reference corrections on the detected data sent from the DAS 20 (Step ST2).

The offset and reference corrections and other such processing are generally called pre-processing because they are conducted before the data is back-projected by a technique such as backprojection to generate image data.

The offset correction refers to a correction of an offset value incorporated into the detected data mainly due to drift of an A–D (analog-to-digital) converter provided in the DAS 20.

The reference correction is for correcting variation in the intensity of X-rays emitted from the X-ray source XL. X-rays emitted from the X-ray source XL do not always have the same intensity, and the intensity of the emitted X-rays may vary under some conditions. In such a case, the ratio dact(ij)/dref(j) between detected data dref(j) from a detector channel ch generally referred to as a reference channel, i.e., a detector channel ch upon which X-rays not passing through the subject 1 always impinge even in the presence of the subject 1, and detected data dact(ij) from other detector channels ch, can be used to correct the variation in intensity of the emitted X-rays.

The reference channel chR is provided at an end of the X-ray detector 70 in the channel direction, and a plurality of the reference channels $ch_R$ are arranged in the column direction, as exemplarily shown in FIG. 2.

The value dpre of the detected data after the processing up to Step ST2 is compared with a predetermined reference value for each detector channel ch (Step ST3).

The reference value is defined as a value obtained from each detector channel ch in the absence of the collimators 50, for example. Then, for example, it may be considered that a value dpre for the detector channel $ch_n$ shown in FIG. 3 is approximately equal to the reference value, and a value dpre for the detector channel $ch_{n+1}$ is smaller than the reference value due to the influence by the portion shadowed by the collimator 50.

To correct the difference in X-ray detection sensitivity among the detector channels ch caused by the presence of the collimators 50 as described above, the calculation/control apparatus 23 creates a sensitivity correction vector based on the value dpre (Step ST4).

Specifically, the calculation/control apparatus 23 calculates a value Vt for transforming the value dpre to the reference value for each detector channel ch, and defines a vector in which the values Vt are arranged in the channel direction for each detector channel row 7 as the sensitivity correction vector.

The sensitivity correction vector does not need to be created for a detector channel row 7 in which the X-ray detection sensitivity is substantially invariant, regardless of the presence of the collimator 50, and the vector is created at least for detector channel rows 7 having the X-ray detection sensitivity varying by the presence of the collimator 50.

As previously discussed, the X-ray detection sensitivity varies with the amount of drift D of the X-ray focal spot 3. Therefore, the calibration process from Step ST1 to Step ST4 is repeated a plurality of times for different amounts of drift D. The calculation/control apparatus 23 then decides whether the calibration process is to be terminated (Step ST5).

The calculation/control apparatus 23 repeats Steps ST1–ST4 until the calibration process is executed for a predetermined number of times for different amounts of drift D. Upon completing the calibration process for the predetermined number of times for different amounts of drift, the calibration is terminated.

The amount of drift D of the X-ray focal spot 3 varies due to, for example, thermal expansion of components in the X-ray source XL as the temperature of the X-ray source XL changes with use.

The value dpre obtained by a reference channel $ch_{R_n}$ in a certain detector channel row 7, such as the detector channel row 7 containing the detector channel $ch_n$ in FIG. 3, in which the X-ray detection sensitivity is invariant and constant, is represented as the value drefpn. Moreover, the value dpre obtained by a reference channel $ch_{R_{n+1}}$ in a certain detector channel row 7, such as the detector channel row 7 containing the detector channel $ch_{n+1}$, in which the X-ray detection sensitivity varies, is represented as the value drefpn+1.

The amount of drift D can be determined according to the magnitude of the ratio Idx=(drefpn+1)/(drefpn).

By using the ratio Idx as an index (argument), a plurality of sensitivity correction vectors for correcting the X-ray detection sensitivity of the detector channels ch in each detector channel row 7 can be obtained according to the indices for that detector channel row 7.

Figure 5:
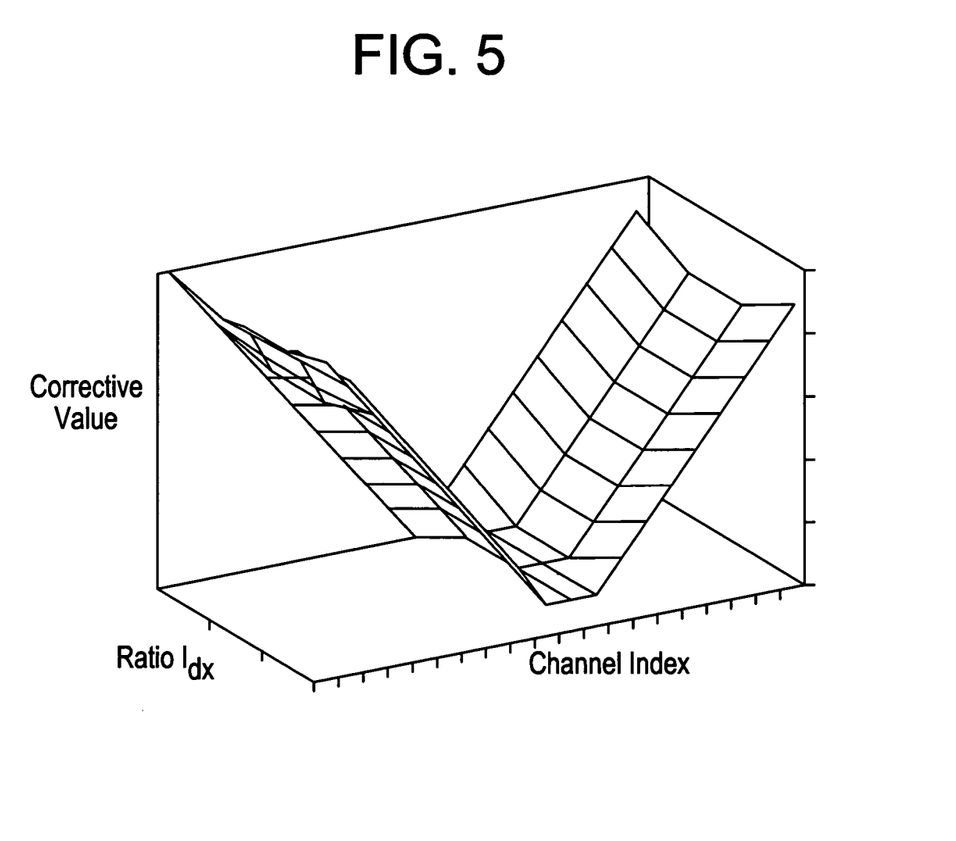
FIG. 5 is a graph representing sensitivity correction vectors for one detector channel row obtained from the calibration, related to the amount of drift of the X-ray focal spot.

FIG. 5 represents the sensitivity correction vectors in one detector channel row 7 as a tri-axial graph.

The first axis in the horizontal direction in FIG. 5 represents the channel index i in the detector channel row 7. The second axis in the depth direction represents the value of the ratio Idx. The third axis in the vertical direction represents a corrective value for transforming the value dpre obtained by each detector channel ch in the target detector channel row 7 into the reference value. These corrective values can be arranged in the sequence of the channel index as elements for generating a vector serving as the sensitivity correction vector.

A sensitivity correction vector for a ratio Idx that cannot be obtained by the processing of Steps ST1–ST 5 is generated by fitting processing such as interpolation or extrapolation. In FIG. 5, the corrective values corresponding to the detector channels ch only for four ratios Idx are shown by connecting them with line segments as an example, though corrective values corresponding to other ratios Idx can be obtained by fitting processing.

Moreover, the number of channel indices i shown in FIG. 5 is merely an example, and data corresponding to a number of corrective values that is the same as the number of the detector channels ch are actually obtained.

These sensitivity correction vectors are, for example, stored in a storage device (not shown), such as a memory or hard disk drive, within the console 10B.

Now a procedure of tomographic imaging on the subject 1 using the X-ray CT apparatus 10 comprising the X-ray detector 70 provided with the aforementioned collimators 50 will be described hereinbelow with reference to the flow chart shown in FIG. 6.

To obtain a tomographic image of the subject 1, projection data of a cross-sectional plane through the subject 1 is first acquired (Step ST10).

As previously discussed, the X-ray source XL and X-ray detector 70 are rotated around the axis O by the rotating section 2 to scan the subject 1, whereby projection data of a cross-sectional plane are obtained in a plurality of views.

The calculation/control apparatus 23 applies first preprocessing such as offset correction, as in the calibration, to the projection data obtained at Step ST10 (Step ST11).

After executing Step ST11, the calculation/control apparatus 23 calculates a ratio Idxr serving as the index for a sensitivity correction vector (Step ST12).

The ratio Idxr is calculated using, for example, values drefrn and drefrn+1 in a first view, corresponding to the aforementioned reference channel $ch_{Rn}$ in which the X-ray detection sensitivity is approximately constant and to the reference channel $ch_{Rn+1}$ in which the X-ray detection sensitivity varies, respectively. The calculation/control apparatus 23 uses these values to calculate the ratio Idxr according to Idxr =(drefrn+1)/(drefrn).

The calculation/control apparatus 23 reads from the storage device a sensitivity correction vector corresponding to the index obtained by the calculation. The calculation/control apparatus 23 uses the read sensitivity correction vector to correct projection data corresponding to each detector channel ch subjected to the processing at Step ST11 (Step ST13).

The calculation/control apparatus 23 corrects the projection data corresponding to each detector channel ch by a calculation of, for example, multiplying a detector channel ch by a corrective value as an element in the sensitivity correction vector, for each detector channel row 7. The value for the corrected projection data is approximately equal to a projection data value obtained by a detector channel ch having approximately the same X-ray detection sensitivity as that in the absence of the collimators 50.

The calculation/control apparatus 23 furthermore applies second pre-processing such as beam hardening (BH) correction to the corrected projection data (Step ST14).

The beam hardening correction is for correcting a nonlinear relationship between the X-ray path length over which X-rays pass through the subject, and detected X-ray intensity, due to a difference in X-ray absorptivity in different materials.

After the processing set forth above, the calculation/control apparatus 23 applies filtering processing preparatory for image reconstruction to the projection data obtained at Step ST14 (Step ST15).

Steps ST11–ST15 are collectively referred to as a preprocessing stage here because they are preparatory processing for image reconstruction processing.

The calculation/control apparatus 23 conducts a calculation for backprojection/image reconstruction using the filtered projection data to generate image data of a predefined cross section through the subject 1 (Step ST16).

Moreover, the calculation/control apparatus 23 conducts post-processing, such as rendering, based on the generated image data (Step ST17).

The post-processing at Step ST17 provides several kinds of processing, such as, for example, color conversion in the tomographic image, or switching between two-dimensional display and three-dimensional display.

A tomographic image based on image data post-processed at Step ST17 is displayed on the display device 25 (Step ST18).

As described above, according to the present embodiment, scatter rays are prevented from reaching the detecting surfaces Su in the X-ray detector 70 by providing the X-ray detector 70 with the collimators 50 each extending in the channel direction, arranged in the column direction.

Moreover, according to the present embodiment, X-ray detection sensitivity of the detector channels ch in the X-ray detector 70 varies due to the provision of the collimators 50, and considering this, a projection data value corresponding to each detector channel ch is corrected. Thus, a tomographic image of the subject 1 can be produced with substantially only the influence by scatter rays removed.

Figure 7A:
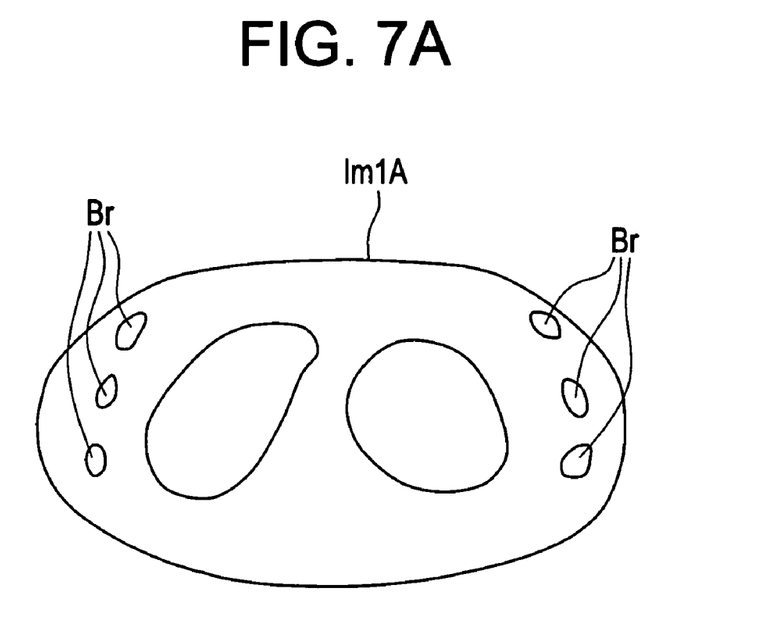
FIG. 7 is a schematic diagram of exemplary tomographic images of a subject, in which (a) shows a tomographic image obtained using the X-ray CT apparatus in accordance with the present embodiment, and (b) shows a tomographic image obtained using a conventional X-ray CT apparatus.
Figure 7B:
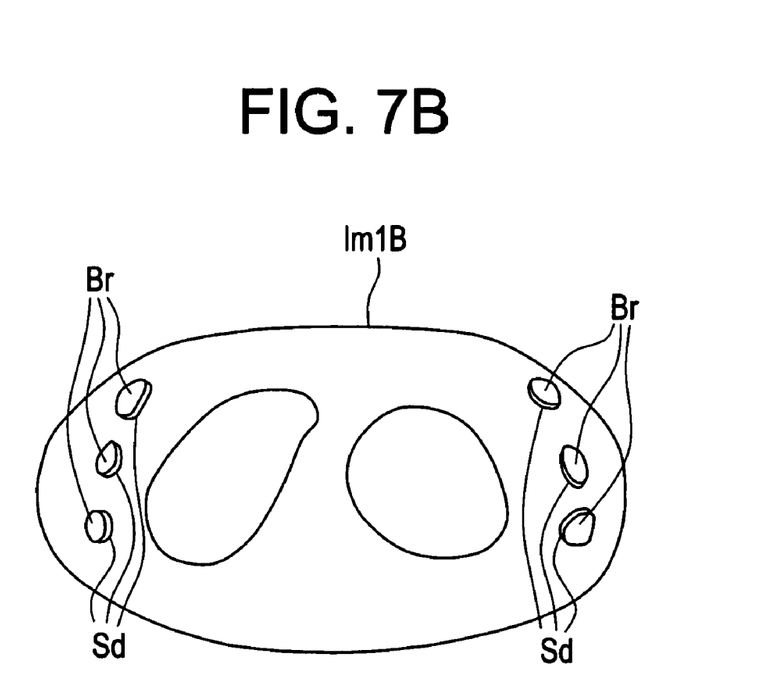

FIGS. 7(a) and (b) are diagrams schematically showing exemplary tomographic images of the subject 1, in which (a) shows a tomographic image Im1A obtained using the X-ray CT apparatus 10 in accordance with the present embodiment, and (b) shows a tomographic image Im1B obtained using a conventional X-ray CT apparatus.

As shown in FIG. 7(b), the conventional apparatus without collimators in the column direction of the X-ray detector for preventing impingement of scatter rays is likely to generate a shade Sd caused by scatter rays at, for example, the border between a bone Br and other tissue. Such a shade Sd is clinically undesirable in that the tomographic image Im1B becomes inaccurate and unclear.

On the other hand, the present embodiment capable of removing the influence by scatter rays provides the tomographic image Im1A without the shade Sd, as shown in FIG. 7(a). Image quality of the tomographic image Im1A without the shade Sd can be considered as being improved over that of the tomographic image Im1B with the shade Sd.

It should be noted that the present invention is not limited to the aforementioned embodiments, and several modifications may be done.

Figure 8:
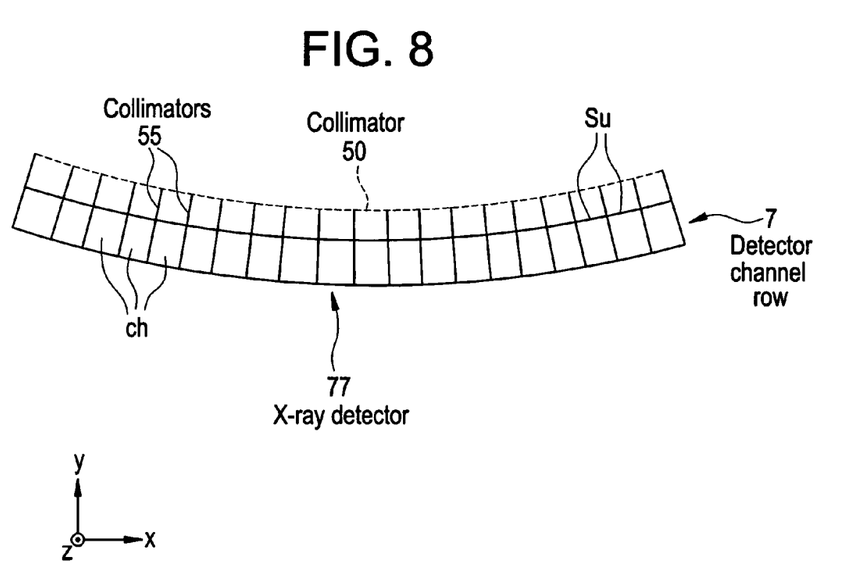
FIG. 8 is a diagram showing an X-ray detector as viewed in the column direction, provided with collimators in both the column and channel directions in accordance with another embodiment of the X-ray detector shown in FIG. 2.

For example, there may be provided not only the collimators 50 but also collimators between detector channels ch adjoining in the channel direction. FIG. 8 is a diagram depicting an X-ray detector 77 as viewed in the column direction (z-axis direction), which comprises, in addition to the collimators 50, collimators 55 extending in the column direction at the borders between the detector channels ch adjoining in the channel direction. The collimators 55 are provided on the side of the detecting surfaces Su, and are directed toward the X-ray focal spot 3, for example. By using the X-ray detector 77 comprising such collimators 55, instead of the X-ray detector 70, the influence by scatter rays are more effectively removed and a tomographic image can be obtained with still higher image quality.

Figure 6:
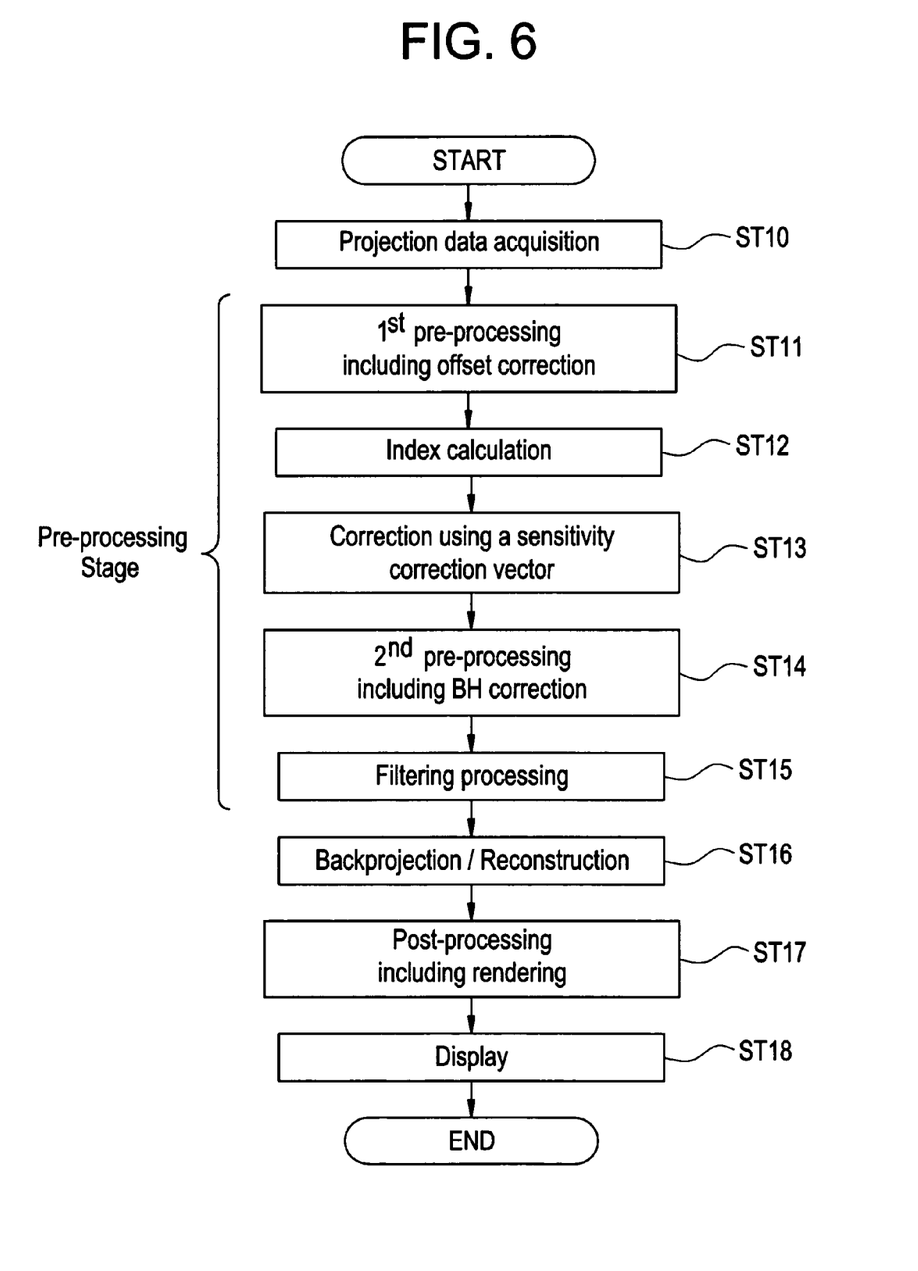
FIG. 6 is a flow chart showing an exemplary procedure of tomographic imaging on a subject using the X-ray CT apparatus shown in FIG. 1.

Moreover, the flow chart shown in FIG. 6 is an exemplary procedure of tomographic imaging, and the index calculation procedure at Step ST12 or the correction procedure at Step ST13 may be executed at any point within the pre-processing stage.

Furthermore, while X-rays are employed as the radiation in the embodiment set forth above, other radiation, such as gamma rays, may be employed.

Many widely different embodiments of the invention may be configured without departing from the spirit and the scope of the present invention. It should be understood that the present invention is not limited to the specific embodiments described in the specification, except as defined in the appended claims.

The invention claimed is:

1. A radiation computed tomographic imaging apparatus comprising:

a radiation source for emitting radiation while rotating around a predefined axis of rotation, wherein said radiation source has an X-ray focal spot;

a radiation detector for detecting said radiation passing through a subject around said axis of rotation, said radiation detector having a plurality of radiation detector elements for detecting said radiation, extending in a two-dimensional manner in first and second arrangement directions, said first arrangement direction being contained in a plane of rotation of said radiation source, said second arrangement direction being orthogonal to said first arrangement direction and aligned along said axis of rotation; and a reconstructing device for arithmetically reconstructing tomographic image data for a tomographic image of said subject based on projection data of said subject obtained from said radiation detected by said radiation detector, wherein said radiation detector comprises collimators for confining an angle at which said radiation impinges upon said radiation detector elements, said collimators being provided at borders between said radiation detector elements adjoining in said second arrangement direction, and wherein a first one of said collimators has a first height determined based on a drift of said X-ray focal spot.

2. The radiation computed tomographic imaging apparatus of claim 1, wherein:

said plurality of radiation detector elements are arranged in said first arrangement direction to form a curve along the direction of rotation of said radiation source, and flatly arranged in said second arrangement direction.

3. The radiation computed tomographic imaging apparatus of claim 1, wherein:

said radiation is emitted from said focal spot of said radiation source;

said radiation source and said radiation detector are disposed symmetrically with respect to a line connecting said focal spot and a midpoint in said second arrangement direction; and said radiation computed tomographic imaging apparatus further comprises a moving device for rotating said radiation source and said radiation detector around said axis of rotation while maintaining their positional relationship relative to each other.

4. The radiation computed tomographic imaging apparatus of claim 3, wherein:

said collimators are provided at positions other than said midpoint in said second arrangement direction.

5. The radiation computed tomographic imaging apparatus of claim 4, wherein:

said collimators are provided at regular intervals in said second arrangement direction.

6. The radiation computed tomographic imaging apparatus of claim 1, wherein:

the first height is determined based on efficiency of radiation usage by at least one of said radiation detector elements.

7. The radiation computed tomographic imaging apparatus of claim 6, wherein:

the first height is smaller than a second height of a second one of said collimators, and wherein said first collimator lying farther from said midpoint in said second arrangement direction than said second collimator.

8. The radiation computed tomographic imaging apparatus of claim 1, wherein:

said radiation detector further comprises said collimators at borders between said radiation detector elements adjoining in said first arrangement direction as well.

9. The radiation computed tomographic imaging apparatus of claim 1, wherein the first height is determined based on a threshold exceeded by an efficiency of X-ray usage of at least one of said radiation detector elements.

10. The radiation computed tomographic imaging apparatus of claim 1, wherein said collimators are located at a position other than a center of said radiation detector.

11. A radiation computed tomographic imaging apparatus comprising:

a radiation source for emitting radiation while rotating around a predefined axis of rotation;

a radiation detector for detecting said radiation passing through a subject around said axis of rotation, said radiation detector having a plurality of radiation detector elements for detecting said radiation, extending in a two-dimensional manner in first and second arrangement directions, said first arrangement direction being contained in a plane of rotation of said radiation source, said second arrangement direction being orthogonal to said first arrangement direction and aligned along said axis of rotation; and a reconstructing device for arithmetically reconstructing tomographic image data for a tomographic image of said subject based on projection data of said subject obtained from said radiation detected by said radiation detector, wherein said radiation detector comprises collimators for confining an angle at which said radiation impinges upon said radiation detector elements, said collimators being provided at borders between said radiation detector elements adjoining in said second arrangement direction, and wherein said reconstructing device corrects a difference in radiation detection sensitivity among said radiation detector elements due to a shadow of said collimators created in emission of a beam of said radiation.

12. The radiation computed tomographic imaging apparatus of claim 11, wherein:

said reconstructing device makes said correction based on a value of a sensitivity correction vector selected based on a ratio between a detected value by a first one of reference channels in which said radiation detection sensitivity varies and a detected value by a second one of reference channels in which said radiation detection sensitivity is invariant, said reference channels being those among said plurality of radiation detector elements that always detect said radiation not passing through said subject.

13. The radiation computed tomographic imaging apparatus of claim 12, wherein:

elements in said sensitivity correction vector have individual values respectively corresponding to said radiation detector elements in said first arrangement direction.

14. A radiation detector for use in a radiation computed tomographic imaging apparatus for generating tomographic image data for a tomographic image of a subject based on projection data of said subject obtained from radiation emitted from a radiation source rotating around a predefined axis of rotation and passing through said subject, wherein said radiation detector comprises:

a plurality of radiation detector elements for detecting said radiation for acquiring said projection data, extending in a two-dimensional manner in first and second arrangement directions, said first arrangement direction being contained in a plane of rotation of said radiation source, said second arrangement direction being orthogonal to said first arrangement direction and aligned along said axis of rotation; and collimators for confining an angle at which said radiation impinges upon said radiation detector elements, provided at borders between said radiation detector elements adjoining in said second arrangement direction, wherein a first one of said collimators has a first height determined based on a drift of an X-ray focal spot of the radiation source.

15. The radiation detector of claim 14, wherein:
said plurality of radiation detector elements are arranged in said first arrangement direction to form a curve along the direction of rotation of said radiation source, and flatly arranged in said second arrangement direction.

16. The radiation detector of claim 14, wherein:
said radiation detector is configured to be symmetric with respect to a line connecting the focal spot of said radiation source and a midpoint in said second arrangement direction; and
said collimators are provided at positions other than said midpoint in said second arrangement direction.

17. The radiation detector of claim 16, wherein:
said collimators are provided at regular intervals in said second arrangement direction.

18. The radiation detector of claim 14, wherein:
the first height is determined based on efficiency of radiation usage by at least one of said radiation detector elements.

19. The radiation detector of claim 18, wherein:
the first height is smaller than a second height of a second one of said collimators, and wherein said first collimator lying farther from said midpoint in said second arrangement direction than said second collimator.

20. The radiation detector of claim 14, further comprising:
said collimators at borders between said radiation detector elements adjoining in said first arrangement direction as well.

* * * * *